US012617840B2

(12) United States Patent
Zhou et al.

(10) Patent No.: US 12,617,840 B2
(45) Date of Patent: May 5, 2026

(54) HYBRIDOMA CELL LINE FOR SECRETING ANTI-RABIES VIRUS M PROTEIN MONOCLONAL ANTIBODY AND APPLICATION THEREOF

(71) Applicant: ZHEJIANG UNIVERSITY, Hangzhou (CN)

(72) Inventors: Jiyong Zhou, Hangzhou (CN); Min Liao, Hangzhou (CN); Yan Yan, Hangzhou (CN); Boli Hu, Hangzhou (CN); Jinyan Gu, Hangzhou (CN); Xiaojuan Zheng, Hangzhou (CN); Weiren Dong, Hangzhou (CN); Yulan Jin, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 1389 days.

(21) Appl. No.: 17/294,414

(22) PCT Filed: Mar. 30, 2020

(86) PCT No.: PCT/CN2020/081974
§ 371 (c)(1),
(2) Date: May 16, 2021

(87) PCT Pub. No.: WO2020/200143
PCT Pub. Date: Oct. 8, 2020

(65) Prior Publication Data
US 2024/0262891 A1      Aug. 8, 2024

(30) Foreign Application Priority Data
Apr. 1, 2019    (CN) .......................... 201910258004.2

(51) Int. Cl.
*C07K 16/10*        (2026.01)
*G01N 33/569*        (2006.01)

(52) U.S. Cl.
CPC ....... *C07K 16/10* (2013.01); *G01N 33/56983* (2013.01); *C07K 2317/34* (2013.01); *G01N 2333/145* (2013.01)

(58) Field of Classification Search
CPC ................ C07K 16/10; C07K 2317/34; G01N 33/56983; G01N 2333/145
See application file for complete search history.

(56) References Cited

U.S. PATENT DOCUMENTS 10,240,131 B2 *    3/2019  Zhou ....................... A61P 31/20

FOREIGN PATENT DOCUMENTS

| | | | | |
|---|---|---|---|---|
| CN | 103954777 A * | 7/2014 | ....... | G01N 33/56983 |
| CN | 104911195 A * | 9/2015 | | |
| EP | 0445625 A1 * | 9/1991 | ............ | C07K 16/10 |
| WO | WO-8909789 A1 * | 10/1989 | ............ | C07K 16/10 |
| WO | WO-2012054502 A1 * | 4/2012 | ............ | C07K 16/10 |
| WO | WO-2020200143 A1 * | 10/2020 | ............ | C07K 16/10 |

OTHER PUBLICATIONS

Guo et al. 2015. CN 104911195 A. Machine translation. (Year: 2015).*
Zhou et al. 2020. WO 2020200143 A1. Machine translation. (Year: 2020).*
Xing. 2014. CN 103954777 A. Machine Translation. (Year: 2014).*
Kazufumi Hiramatsu et al., "Mapping of he anitgenic determinants recognized by monoclonal antibodies against the M2 protein of rabies virus" Virology, vol. 187, No. 2, Apr. 30, 1992, pp. 472-479.

* cited by examiner

*Primary Examiner* — Michael Allen
*Assistant Examiner* — Carey Alexander Stuart
(74) *Attorney, Agent, or Firm* — Jiwen Chen; Joywin IP Law PLLC

(57)        ABSTRACT
The present invention is a hybridoma cell line for secreting monoclonal antibody against rabies virus M protein and its application, relates to the field of biotechnology. A classification of the hybridoma cell line is named as hybridoma cell line 4A1, and the hybridoma cell line was deposited on Apr. 1, 2019 in the China Center for Type Culture Collection, Wuhan University, Wuhan, China, with a deposit number CCTCC NO: C201947. The monoclonal antibody prepared by the hybridoma cell line has high titer, good specificity and excellent biological characteristics. The present invention identifies the variant antigen epitope recognized by the RABV M protein, the hybridoma cell line can be used to distinguish Flury strain and other RABV strains, prepare kit for detecting rabies virus RABV, detect RABV infection and differential diagnosis vaccine Flury strain and other RABV strains.

3 Claims, 3 Drawing Sheets
(3 of 3 Drawing Sheet(s) Filed in Color)
Specification includes a Sequence Listing.

Flury &
Variant
Strains (SEQ ID NO: 40)
(SEQ ID NO: 41)
(SEQ ID NO: 42)
(SEQ ID NO: 43)
(SEQ ID NO: 44)
(SEQ ID NO: 45)
(SEQ ID NO: 46)
(SEQ ID NO: 47)
(SEQ ID NO: 48)
(SEQ ID NO: 49)
(SEQ ID NO: 50)
(SEQ ID NO: 51)
(SEQ ID NO: 52)
(SEQ ID NO: 53)
(SEQ ID NO: 54)
(SEQ ID NO: 55)
(SEQ ID NO: 56)
(SEQ ID NO: 57)
(SEQ ID NO: 58)
(SEQ ID NO: 59)
(SEQ ID NO: 60)
(SEQ ID NO: 61)
(SEQ ID NO: 62)
(SEQ ID NO: 63)
(SEQ ID NO: 64)
(SEQ ID NO: 65)
(SEQ ID NO: 66)
(SEQ ID NO: 67)
(SEQ ID NO: 68)
(SEQ ID NO: 69)
(SEQ ID NO: 70)
(SEQ ID NO: 71)
(SEQ ID NO: 72)

| F1: | $^{25}$PPYDDD$^{30}$ | (SEQ ID NO: 1) |
| F2: | $^{25}$PLYDDD$^{30}$ (P26L) | (SEQ ID NO: 38) |
| F3: | $^{25}$PPDDDD$^{30}$ (Y27D) | (SEQ ID NO: 2) |
| F4: | $^{25}$PPYGDD$^{30}$ (D28G) | (SEQ ID NO: 39) |

HYBRIDOMA CELL LINE FOR SECRETING ANTI-RABIES VIRUS M PROTEIN MONOCLONAL ANTIBODY AND APPLICATION THEREOF

This is a U.S. national stage application of PCT Application No. PCT/CN2020/081974 under 35 U.S.C. 371, filed Mar. 30, 2020 in Chinese, claiming priority of Chinese Application No. 201910258004.2, filed Apr. 1, 2019, all of which is hereby incorporated by reference.

TECHNICAL FIELD

The present invention relates to the field of biotechnology, in particular to hybridoma cell line for secreting anti-rabies virus M protein monoclonal antibody and use thereof.

DESCRIPTION OF RELATED ART

Rabies is a highly lethal zoonotic disease caused by the rabies virus (RABV). After the onset of RABV infection, the fatality rate is almost 100%, which is by far the acute infectious disease with the highest mortality rate in human history. There are still no treatments, and only vaccines can be used to prevent RABV infection. Rabies cases have been reported in more than 150 countries around the world. About 50,000 to 70,000 people die from rabies every year, 95% of rabies cases occur in Africa and Asia. The number of human rabies infections in China is second only to India and the second largest in Asia. Dogs are the most common virus reservoir of RABV, and 99% of human infections with rabies are mediated by canine transmission.

RABV belongs to the Rhabdoviridae rabies virus genus (Lyssavirus) in virus taxonomy. It is a single-stranded non-segmented RNA virus. Its genome mainly encodes nucleo-protein (N), phosphoprotein (P), matrix protein (M), glyco-protein (G) and RNA-dependent RNA polymerase protein (L). M protein is composed of 202 amino acids and about 23 kDa, and is the smallest and most abundant non-glycosy-lated protein of RABV virus particles. The M protein is located between the viral envelope and the nucleocapsid and serves to connect the G protein and the nucleus. The M protein has multiple functions: participating in the assembly and budding of virus particles, playing a decisive factor in the shape of virus particles, regulating the transcription and translation process of the virus, participating in determining the pathogenicity of the virus, inducing cell apoptosis, and inhibiting the expression of host-related genes, etc.

The monoclonal antibodies against RABV proteins that have been prepared are mainly NP protein and G protein. Monoclonal antibody to NP protein can be used to distin-guish different serotypes of rabies virus; Monoclonal anti-body to G protein shows a higher neutralizing activity. There are few reports on the monoclonal antibody anti-RABV M protein, and the fine epitopes recognized by the monoclonal antibody to RABV M protein are still unclear, and lacking understanding of the biological characteristics of these monoclonal antibodies, so the application in virus diagnosis of anti-M protein monoclonal antibodies and research on the structure and antigenic properties of M protein are restricted.

SUMMARY OF THE INVENTION

The object of the present invention is to provide a hybridoma cell line for secreting a monoclonal antibody that specifically recognizes a RABV M protein, and the monoclonal antibody can specifically react with RABV field strain but not with the vaccine Flury strain.

In order to achieve the above object, the present invention adopts the following technical solutions:

A hybridoma cell line for secreting monoclonal antibody to rabies virus M protein, a classification of the hybridoma cell line is named as hybridoma cell line 4A1, and the hybridoma cell line was deposited on Apr. 1, 2019 in the China Center for Type Culture Collection, Wuhan Univer-sity, Wuhan, China, with a deposit number CCTCC NO: C201947.

The present invention first obtains 12 strains of hybridoma cells stably secreting monoclonal antibody to RABV M protein, and finally screens out the hybridoma cell 4A1 strain, which has excellent biological characteristics. The titer of the prepared monoclonal antibody 4A1 in mouse ascites was $1\times10^5$ measured by indirect enzyme-linked immunosorbent assay.

The present invention also provides a monoclonal anti-body to rabies virus M protein prepared from the hybridoma cell 4A1 strain.

The present invention identifies the variant antigen epitopes recognized by the monoclonal antibody for the first time, and its amino acid sequences are shown in SEQ ID NO:1 and SEQ ID NO:2. These epitopes are relatively conserved on the M protein of different RABV strains, but there is an antigenic variation on the vaccine Flury strain (the amino acid sequence of the Flury strain is shown in SEQ ID NO: 3), which makes the monoclonal antibody unable to recognize the epitope. Therefore, the monoclonal antibody provided by the present invention can specifically react with the rabies virus strain, but cannot react with the vaccine Flury strain.

The present invention provides an application of the hybridoma cell 4A1 strain in preparing a kit for detecting RABV. The hybridoma cell 4A1 strain can be applied to the methods such as ELISA, immunofluorescence, Western Blot, immunohistochemistry, etc., and can be used in the preparation of reagents for clinical diagnosis of RABV infection, or in the detection of the pathogen of RABV that is not for the purpose of diagnosis application.

The present invention provides an application of the monoclonal antibody in preparing a kit for detecting rabies virus RABV. The monoclonal antibody can be applied to methods such as ELISA, immunofluorescence, Western Blot, immunohistochemistry, etc., and can be used in the preparation of reagents for clinical diagnosis of RABV infection, or in the detection of the pathogen of RABV that is not for the purpose of diagnosis application.

The present invention also provides a kit for detecting rabies virus RABV, the kit includes the monoclonal antibody to rabies virus M protein.

The beneficial effects of the present invention: the mono-clonal antibody 4A1 secreted by the hybridoma cell 4A1 strain can specifically react with RABV strain, but cannot react with the Flury strain; the monoclonal antibody pro-vided by the present invention can be used for preparation kits of ELISA, immunofluorescence, Western Blot, immu-nohistochemistry and other methods, and can be used for the clinical detection of RABV or the differential diagnosis of Flury strain and other strains.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figures 1, 2:
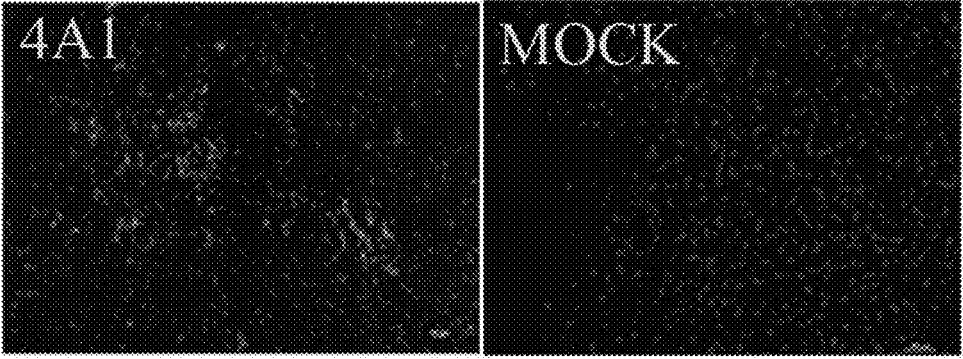
FIG. 1 shows specificity of the monoclonal antibody.
FIG. 2 shows a comparison of the epitopes recognized by the monoclonal antibody in different RABV strains with, from the top to bottom sequentially, SEQ ID NO: 40 to SEQ ID NO: 72.

In the following, the present invention will be further described in conjunction with the embodiments.

Embodiment 1

(First) Establishment of a Hybridoma Cell Line Secreting a Monoclonal Antibody

1. Prokaryotic Expression and Purification of CVS-11 M Protein

Specific primers were designed based on the nucleotide sequence of the gene encoding M protein (sequence number: ADJ29910.1) of the CVS-11 (Liu Juan, et al. BECN1-dependent CASP2 incomplete autophagy induction by binding to rabies virus phosphoprotein. Autophagy, 2017, 13(4): 739-753) strain registered in GenBank. Using the extracted viral RNA reverse transcription product as a template, the M gene of RABV was amplified, and then the M gene was cloned into the pET-28a(+) vector. After the correct sequencing was verified, the competent cell *E. coli* BL21 (DE3) was transformed, and the recombinant M protein was purified with a Ni-NTA column (purchased from QiAGEN) after induction with IPTG (1 mM) at 37° C. for about 5 hours. The expression and purification of recombinant M protein were analyzed by sodium dodecyl sulfate-polyacrylamide gel electrophoresis (SDS-PAGE) and Western blot.

2. Animal Immunization

Using the above purified M protein as an immunogen, female BALB/c mice aged 6~8 weeks (purchased from Shanghai Xipuer-Bikai Experimental Animal Co., Ltd.) were injected subcutaneously into the back of the mice with dose of 100 μg recombinant M protein per mouse. For the first immunization, an equal volume of Freund's adjuvant complete (purchased from Sigma) was used to emulsify the antigen, and then every 14 days, Freund's adjuvant incomplete (purchased from Sigma) was used to emulsify the antigen for two booster immunizations. One week after the third immunization, blood was collected from the tail and the serum antibody titer was determined. Mice with serum antibody titer>$10^6$ were selected and re-boosted the immunization (200 μg/mouse) by intraperitoneal injection of antigen without adjuvant 3 days before cell fusion.

3. Cell Fusion

Using a method of PEG cell fusion. Myeloma cells SP2/0 and BALB/c mouse spleen cells that have been immunized were fully mixed at a ratio of 1:10, and then 1 mL 50% PEG-4000 (purchased from Sigma) preheated to 37° C. was added within 1 min, then it was shaken gently while adding, and then it was allowed to stand for 1 min. Serum-free RPMI-1640 (purchased from Hyclone) medium preheated to 37° C. was added along the tube wall to terminate the fusion reaction. It was required to add 4 mL in the first minute, add 1 mL in the first 30 seconds, and 3 mL in the next 30 seconds; add 11 mL in the second minute, and add to the total volume of 40 mL in the last 3 minutes. After centrifugation at 1000 rpm for 5 min, the supernatant was discarded, and then 30 ml RPMI-1640 incomplete medium was added along the tube wall. The supernatant was centrifuged and discarded again to remove the residual fusion agent PEG as much as possible. A 40 mL of complete medium containing HAT (purchased from Sigma) and 10% FBS (purchased from Gibco) pre-warmed to 37° C. were added along the wall of the 50 mL centrifuge tube, and pipette gently to resuspend the cells. Then the resuspended cells were transferred to a 10 cm cell culture dish, the mixed cells were inoculated at 100 μL/well into a 96-well cell culture plate with feeder cells, and then the cell culture plate was placed in a cell culture box (purchased from Thermo) at 37° C. and 5% $CO_2$ for static culture. After 5 days, RPMI-1640 (purchased from Hyclone) medium containing HT (purchased from Sigma) and 10% FBS (purchased from Gibco) was used, and after 10 days, RPMI-1640 medium (purchased from Hyclone) containing 10% FBS (purchased from Gibco). When the fused cells grow to $\frac{1}{10}$-$\frac{1}{5}$ of the bottom of the 96-well plate, the culture supernatant was taken to detect the antibody.

4. Screening of Hybridoma Cells

The purified M protein was diluted with 0.05 mol/L carbonate buffer (pH 9.6), then an ELISA plate (100 μL/well) was wrapped with 0.02 mg/mL M protein, and then wrapped at 4° C. overnight (not less than 12 hours), washed with PBST solution 3 times, 5 minutes each time, and dried after the third time. The ELISA plate was blocked with PBS containing 10% skimmed milk powder (200 μL/well), placed at 37° C. for 1 hour, washed with PBST solution 3 times, 5 minutes each time, and dried after the third time. The supernatant of 14 days after fusion, positive serum of 1:1000 dilution immunized mice and negative serum of 1:1000 dilution immunized mice were added into the corresponding well (100 μL/well), treated at 37° C. for 1 hour, washed with PBST for 3 times, 5 min each time, and dried after the third time. A 1:10000 diluted horseradish peroxidase (HRP) labeled goat anti-mouse IgG (purchased from KPL) skimmed milk powder was added (100 μL/well), treated at 37° C. for 1 hour, washed with PBST for 3 times, 5 min each time, and dried after the third time. A substrate TMB-$H_2O_2$ (100 μL/well) was added, treated at 37° C. and protected from light for 10 min, and 50 μL sulfuric acid (2 mol/L) was added to each well to stop the reaction. The microplate reader was zeroed with a blank control, and the OD450 nm value of each well was measured, where P was the OD450 nm value of the sample in the well to be tested, and N was the OD450 nm value of the negative reference serum, so that N≤0.1, the ratio of the OD450 nm value of the positive reference serum to the OD450 nm value of the negative reference serum is ≥2.1, that is, under the premise that the negative and positive controls were established, the test well with P/N≥2.1 was judged as positive, the test well with 2.1>P/N≥1.5 was judged as suspicious, and the test well with P/N<1.5 was judged as negative. Finally, the test was repeated after 3 days, and the hybridoma cell lines with positive test results for both times were selected for cloning.

5. Cloning of Hybridoma Cells

First, the live cells in the positive wells were stained and counted with trypan blue, and then diluted with RPMI-1640 medium (purchased from Hyclone) containing 10% FBS (purchased from Gibco) into 100 cells/10 mL medium cells suspension, and then the diluted cell suspension was added to a 96-well cell culture plate (100 μL/well) covered with feeder cells and placed at 37° C. with 5% $CO_2$ incubator. Observing the formation of cloned cells every day under an optical microscope, at the same time recording the growth of a single clone, and taking the cell supernatant for ELISA detection when the cells grow to $\frac{1}{10}$-$\frac{1}{5}$ of the bottom of the 96-well plate. The monoclonal cells with positive test results were selected and cloned again, until the supernatant of all cell wells from single cloned cell were positive, the wells with the largest OD450 nm value were selected for expansion and culture. Finally, 12 strains hybridoma cells stably secreting RABV-specific monoclonal antibodies were screened from the hybridoma cell bank.

6. Preparing of RABV Monoclonal Antibody

Female BALB/c mice (purchased from Shanghai Xipuer-Bikai Experimental Animal Co., Ltd.) at the age of 6-8 weeks were intraperitoneally injected with 0.5 ml/mouse sterilized liquid paraffin. After 7 days, the hybridoma cell line (0.5 mL/mouse, containing $2\times10^6$~$5\times10^6$ hybridoma cells) was injected into the abdominal cavity of the mice. Then after 7-10 days, the abdomen of the mice with obvious bulge was taken to centrifuge at 5000 rpm for 10 min and the supernatant was collected as RABV monoclonal antibody and stored at −20° C.

(Second) Biological Characteristics of Monoclonal Antibody 4A1

(2) Biological Characteristics of Monoclonal Antibody 4A1 Biological Collection of Monoclonal Antibody 4A1

Hybridoma cell line 4A1 was deposited in the China Type Culture Collection on Apr. 1, 2019, address: Wuhan University, Wuhan, China, and the deposit number is CCTCC NO: C201947. The classification designation: Hybridoma cell line 4A1.

1. Determination of the Type of Monoclonal Antibody

The subclass determination was performed using the operating instructions of the monoclonal antibody subclass identification kit (purchased from Thermo). The results showed that the subtype of monoclonal antibody 4A1 was IgG2bκ.

2. Determination of Titer and Stability of Monoclonal Antibodies

The hybridoma cell line 4A1 for secreting monoclonal antibody was continuously cultured and passaged 20 times, cryopreserved in liquid nitrogen and resuscitated. The purified prokaryotic expression of RABV M protein was used as a detection antigen. The indirect ELISA method was used to continuously detect the titer of monoclonal antibody 4A1. The results showed that the ELISA titer of the antibody secreted by hybridoma cells of each generation was basically the same, reaching $10^3$-$10^4$.

3. Specific Identification of Monoclonal Antibodies

Indirect immunofluorescence test was used to verify the reactivity of monoclonal antibody 4A1 with RABV. BHK-21 cells (purchased from ATCC) were infected with CVS-11 strain, the cell culture medium was sucked and discard after culturing for 48 hours, and −20° C. pre-cooled methanol-acetone (1:1) fixative, 200 uL/well was added. After 15 minutes of fixation at −20° C., the fixed solution was discarded, washed with PBS for 3 times, and then dried. Then adding 5% skimmed milk powder (200 uL/well), blocking at 37° C. for 1 hour, washing again with PBST 3 times, then adding monoclonal antibody 4A1 (1:500), incubating at 37° C. for 1 hour, and washing again with PBS 3 times, patting dry and then adding 1:500 diluted FITC-labeled goat anti-mouse IgG antibody (purchased from KPL), incubating at 37° C. for 1 hour, washing 3 times with PBS, and patting dry. Furthermore adding 50 uL of PBS to each well and placing under a fluorescence microscope for observation. The results showed that monoclonal antibody 4A1 produced green fluorescence after reacting with CVS-11 infected BHK-21 cells. While monoclonal antibody 4A1 did not produce green fluorescence after reacting with BHK-21 cells uninfected with CVS-11 strain (see FIG. 1).

4. Identification of Epitopes Recognized by Monoclonal Antibodies

The 609 bp sequence (aa1-aa203) of the M protein gene was divided into overlapping fragments, and primers were designed (Table 1). Hind III/Kpn I restriction sites were introduced into upstream and downstream respectively. The amplified and purified target fragment was cloned into the expression vector pET-28a (+) to construct a recombinant plasmid. After that, the competent cell *E. coli* BL21 (DE3) was transformed, and the recombinant His tag polypeptide and monoclonal antibody were confirmed by Western blot. The positive segment was gradually truncated and expressed to complete the preliminary positioning of the antigen epitope. In order to accurately identify the epitope, primers were designed gradually from the N-terminus and C-terminus of the preliminarily positioned peptides in units of 1 amino acid residue, and BamH I/Xho I restriction sites were introduced upstream and downstream respectively (Table 2). The target fragment was obtained by annealing the upstream and downstream primers, and the target fragment was cloned into the expression vector pGEX-4T-1 to construct a recombinant plasmid, and transformed into competent cells *E. coli* BL21 (DE3). Western blot was used to detect the reactivity of the induced recombinant GST polypeptide with the monoclonal antibody, and the epitope recognized by the monoclonal antibody was determined to be $^{25}$PPYDDD$^{30}$ (SEQ ID NO. 1).

TABLE 1

| | | |
|---|---|---|
| Primers for confirmation of the location of the epitopes recognized by the monoclonal antibodies | | |

| Amino acid position | Primer name | Primer sequence (5'-3') |
|---|---|---|
| 1-203 aa | MF | ggggtaccatgaacgttctacgcaagat (Hind III) (SEQ ID NO. 4) |
| | MR | cccaagctttttattctagaagcagagaagag (Kpn I) (SEQ ID NO. 5) |
| 1-107 aa | M-BW1F/MF | ggggtaccatgaacgttctacgcaagat (Hind III) (SEQ ID NO. 6) |
| | M-BW1R | cccaagcttaggtactggagctcctgataaa (Kpn I) (SEQ ID NO. 7) |

TABLE 1-continued

Primers for confirmation of the location of the
epitopes recognized by the monoclonal antibodies

| Amino acid position | Primer name | Primer sequence (5'-3') |
|---|---|---|
| 101-203 aa | M-BW2FF | ggggtaccttatcaggagctccagtacct (Hind III) (SEQ ID NO. 8) |
| | M-BW2R/MR | cccaagctttttattctagaagcagagaagag (Kpn I) (SEQ ID NO. 9) |
| 1-32 aa | M-BW3F/MF | ggggtaccatgaacgttctacgcaagata (Hind III) (SEQ ID NO. 10) |
| | M-BW3R | cccaagcttccacaggtcatcgtcatacgg (Kpn I) (SEQ ID NO. 11) |
| 26-36 aa | M-BW4F | ggggtaccccgtatgacgatgacctgtggettccacctcct (Hind III) (SEQ ID NO. 12) |
| | M-BW4R | cccaagcttaggaggtggaagccacaggtcatcgtcatacgg (Kpn I) (SEQ ID NO. 13) |
| 33-203 aa | M-BW5F | ggggtacctgacctgtggcttccacctc (Hind III) (SEQ ID NO. 14) |
| | M-BW5R/MR | cccaagctttttattctagaagcagagaagag (Kpn I) (SEQ ID NO. 15) |
| 1-17 aa | M-BW3.1F/M | ggggtaccatgaacgttctacgcaagata (Hind III) (SEQ ID NO. 16) |
| | M-BW3.1R | tagggatgaggacactcaaaagcttggg (Kpn I) (SEQ ID NO. 17) |
| 17-32 aa | M-BW3.2F | ggggtacccaaaagccctctcctgtgt (Hind III) (SEQ ID NO. 18) |
| | M-BW3.2R | cccaagcttccacaggtcatcgtcatacgg (Kpn I) (SEQ ID NO. 19) |

TABLE 2

Primers for fine mapping of the epitopes
recognized by the monoclonal antibodies

| Amino acid position | Primer name | Primer sequence (5'-3') |
|---|---|---|
| 24-32 aa | M-BW3.2.1F | cgcccctccgtatgacgatgacctgtgga (SEQ ID NO. 20) |
| | M-BW3.2.1R | catggcggggaggcatactgctactggacaccttcga (SEQ ID NO. 21) |
| 24-31 aa | M-BW3.2.2F | gatccgcccctccgtatgacgatgacctgc (SEQ ID NO. 22) |
| | M-BW3.2.2R | tcgagcaggtcatcgtcatacggagggggcg (SEQ ID NO. 23) |
| 24-30 aa | M-BW3.2.3F | gatccgcccctccgtatgacgatgacc (SEQ ID NO. 24) |
| | M-BW3.2.3R | tcgaggtcatcgtcatacggagggggcg (SEQ ID NO. 25) |
| 24-29 aa | M-BW3.2.4F | gatccgcccctccgtatgacgatc (SEQ ID NO. 26) |
| | M-BW3.2.4R | tcgagatcgtcatacggagggggcg (SEQ ID NO. 27) |
| 24-28 aa | M-BW3.2.5F | gatccgcccctccgtatgacc (SEQ ID NO. 28) |
| | M-BW3.2.5R | tcgaggtcatacggagggggcg (SEQ ID NO. 29) |
| 25-32 aa | M-BW3.2.6F | gatcccctccgtatgacgatgacctgtggc (SEQ ID NO. 30) |
| | M-BW3.2.6R | tcgagccacaggtcatcgtcatacggaggg (SEQ ID NO. 31) |
| 26-32 aa | M-BW3.2.7F | gatcccgtatgacgatgacctgtggc (SEQ ID NO. 32) |
| | M-BW3.2.7R | tcgagccacaggtcatcgtcatacggg (SEQ ID NO. 33) |
| 27-32 aa | M-BW3.2.8F | gatcctatgacgatgacctgtggc (SEQ ID NO. 34) |
| | M-BW3.2.8R | tcgagccacaggtcatcgtcatag (SEQ ID NO. 35) |

TABLE 2-continued

| Primers for fine mapping of the epitopes recognized by the monoclonal antibodies | | |
| --- | --- | --- |
| Amino acid position | Primer name | Primer sequence (5'-3') |
| 28-32 aa | M-BW3.2.9F | gatccgacgatgacctgtggc (SEQ ID NO. 36) |
| | M-BW3.2.9R | tcgagccacaggtcatcgtcg (SEQ ID NO. 37) |

5. Analysis of Monoclonal Antibody Epitope Sequence

Figure 3:
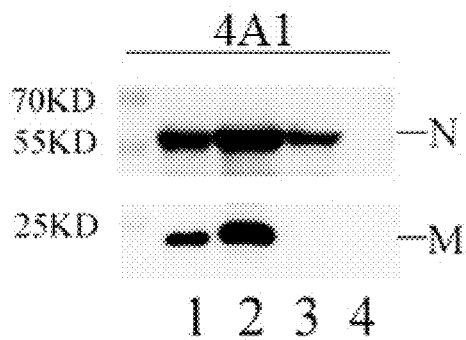
FIG. 3 shows a reactivity of the monoclonal antibody with different strains.
Figure 4:
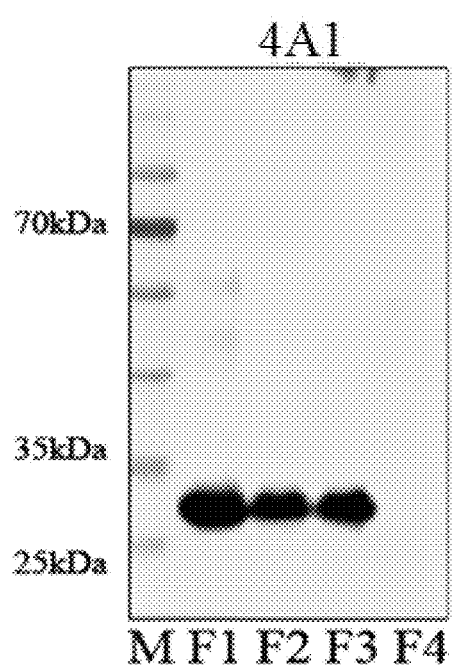
FIG. 4 shows a reactivity of the monoclonal antibody with different mutant epitopes, including $^{25}$PPYDDD$^{30}$ (SEQ ID NO: 1), $^{25}$PLYDDD$^{30}$ (SEQ ID NO: 38), $^{25}$PPDDDD$^{30}$ (SEQ ID NO.2), $^{25}$PPYGDD$^{30}$ (SEQ ID NO: 39).

The identified epitope sequence [25]PPYDDD[30] (SEQ ID NO. 1) was compared with the amino acid sequence of the M protein of the RABV strain registered by NCBI (FIG. 2), the results showed that the epitope was mainly [25]PPDDDD[30] (SEQ ID NO. 2) sequence in RABV strain. After that, the mutation of amino acid P26L and Y27D were detected by Western blot, the results showed that the monoclonal antibody could still react with the mutation of amino acid P26L and Y27D, indicating that the monoclonal antibody 4A1 recognized the epitope of the CVS-11 strain replaced by Y27D, but the antigenicity of epitope was not affected (FIG. 4). At the same time, Western blot test results showed that the M protein monoclonal antibody of the present invention can react with CVS-11 and WT strains, but not with the HEP-Flury strain (purchased from the Chinese Veterinary Microbial Culture Collection and Management Center, deposit number: CVCC AV2013) (FIG. 3). In addition, the monoclonal antibody to N protein of the RABV strain can react specifically with three strains, which showed that the virus infected the cells successfully. Furthermore, through RABV sequence comparison, it was found that the epitope sequence of the HEP-Flury strain was [25]PPDGDD[30] (SEQ ID NO. 3), and the [25]PPYDDD[30] (SEQ ID NO. 1) epitope was further mutated with amino acid D28G, and Western blot found that the monoclonal antibody 4A1 could not recognize it (FIG. 4). However, the epitope identified in the present invention and Flury and its variant strains undergo amino acid D28G mutation (FIG. 2: HEP-Flury, rHEP5.0-CVSG, LEP-Flury, Flury-LEP-C), which affected the epitope. Therefore, the monoclonal antibody of the present invention can also be used to distinguish Flury and variant strains from other popular RABV strains.

6. Immunohistochemistry of Monoclonal Antibodies

C57BL/6 mice aged 6-8 weeks (purchased from Shanghai Xipuer-Bekay Laboratory Animal Co., Ltd.) were intracranially infected with 30 uL CVS-11 strain ($10^5$TCID$_{50}$/mL) and HEP-Flury strain, when the symptoms were obvious, the mice were anesthetized with 2.5% avertin (purchased from sigma), and then the brains were taken. The same volume of DMEM was intracranially injected as a blank control.

(1) Fixation and embedding: fixed with 4% paraformaldehyde for 24 hours, then dehydrated and transparent with alcohol, then immersed in paraffin for embedding, and finally sectioned.

(2) Paraffin wax was deparaffinized to water after sectioning: putting the sections in xylene I for 15 minutes, xylene II for 15 minutes, xylene III for 15 minutes, absolute ethanol I for 5 minutes, and absolute ethanol II for 5 minutes, 85% alcohol for 5 minutes, 75% alcohol for 5 minutes, and finally washing with distilled water.

(3) Antigen retrieval: placing the tissue section in a retrieval box filled with citric acid antigen retrieval buffer (pH 6.0) (purchased from Fuzhou Maixin Biotechnology Development Company), and placing it in a microwave oven for 5 minutes at medium heat, and stopping the fire for 5 minutes, and turning to low heat for 10 minutes for antigen retrieval. During this process, the buffer should be prevented from over-evaporating, and the film should not be dried. After natural cooling, the slides were washed 3 times in PBS (pH 7.4) for 5 min each time.

(4) Blocking endogenous peroxidase: putting the slices in 3% hydrogen peroxide solution, incubating at room temperature for 25 min in the dark, and then washing the slides in PBS (pH 7.4) for 3 times, 5 min each time.

(5) Serum blocking: dropping 3% BSA (purchased from Servicebio) into the histochemistry circle to evenly cover the tissue, and blocking for 30 min at room temperature.

(6) Adding the primary antibody: First the blocking solution was gently shaken off, and the primary antibody (monoclonal antibody of the present invention) diluted 1:500 was dropped on the CVS-11 strain, HEP-Flury strain and DMEM infected brain tissue sections. The sections were placed flat in a wet box and incubated overnight at 4° C. (a small amount of water was added to the wet box to prevent the antibody from evaporating). Among them, the HEP-Flury strain infected brain tissue slices were used as a positive control. The slices used the serum of HEP-Flury infected mice as the primary antibody.

(7) Adding secondary antibody: Slides were washed in PBS (pH 7.4) for 3 times and 5 min each time. After the sections were dried slightly, HRP-labeled goat anti-mouse IgG (purchased from KPL) was added dropwise to cover the tissue in the circle, and incubated at room temperature for 50 min.

(8) DAB color development: The slides were washed 3 times in PBS (pH 7.4) and 5 min each time. After the slices were dried slightly, adding freshly prepared DAB color developing solution (purchased from Fuzhou Maixin Biotechnology Development Company) was added into the circle, controlling the color development time under the microscope, and the positive was brown-yellow, and finally washing the slices with tap water to stop the color development.

(9) Re-staining nucleus: Hematoxylin re-stained the nucleus for about 3 minutes, and then washing with tap water. After the hematoxylin differentiation solution differentiated for a few seconds, washing with tap water again, and waiting until the hematoxylin blue solution returns to blue. Finally washing again with running water.

(10) Dehydration and mounting: putting the slices in 75% alcohol for 5 minutes, 85% alcohol for 5 minutes, absolute ethanol I for 5 minutes, absolute alcohol II for 5 minutes, and xylene I for 5 minutes to make the slices dehydrated and transparent. Then taking the slices out of xylene to dry a little, and finally covering the slices with neutral gum.

Figure 5:
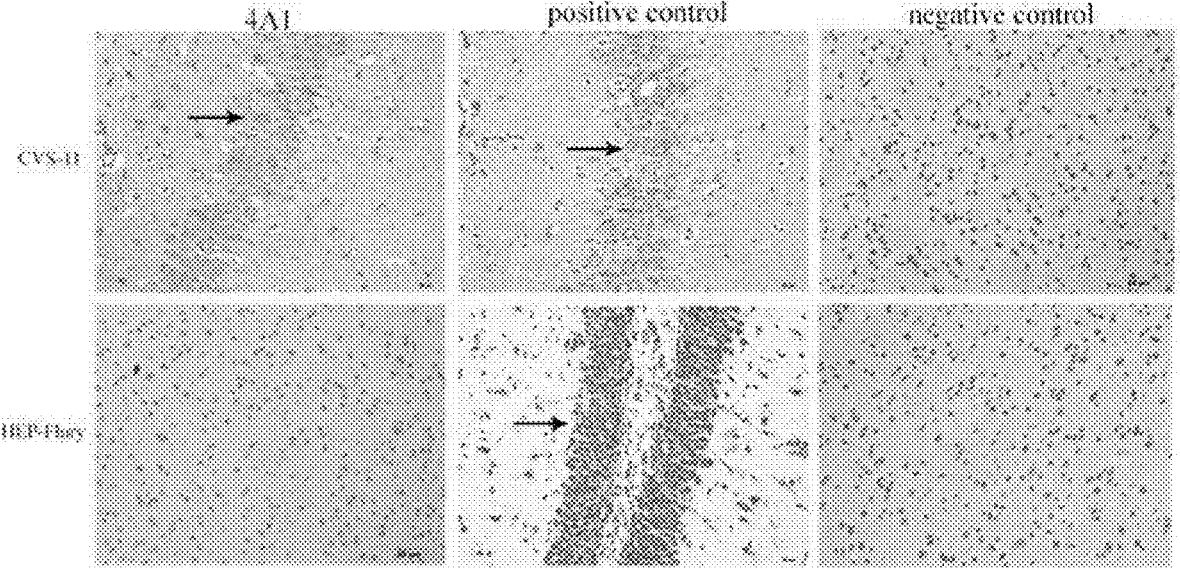
FIG. 5 shows an immunohistochemistry reaction of a monoclonal antibody.

(11) Perform microscopic examination: the results of image acquisition and analysis showed that the hematoxylin-stained cell nucleus was blue, and the positive expression of DAB was brown, which indicated that the monoclonal antibody could label the RABV virus in the infected brain tissue (FIG. 5).

An amended Sequence Listing in ASCII text file (CRF format) with the file name of P76149US0_SEQ_LIST_amdt_12_2025_ST25.txt, created on Dec. 28, 2025 and with the size of 22,211 bytes is incorporated into the specification by reference. It is respectfully submitted that the Sequence Listing in CRF format does not include new matter. In addition, the Sequence Listings hereby submitted satisfy both the paper copy requirement under 37 CFR 1.821(c) and the computer-readable form requirement of 37 CFR 1.182(e). Thus, the requirement of 37 CFR 1.821(f) has been satisfied.

The invention claimed is:

1. A hybridoma cell line for secreting a monoclonal antibody against rabies virus M protein, wherein the classification designation of the hybridoma cell line is Hybridoma cell line 4A1 with a deposit number of the Hybridoma cell line China Center for Type Culture Collection (CCTCC) NO: C201947.

2. A monoclonal antibody against rabies virus M protein, wherein the monoclonal antibody is prepared from the hybridoma cell line according to claim 1.

3. A kit for detecting rabies virus, comprising the monoclonal antibody against rabies virus M protein according to claim 2.

* * * * *

SEQUENCE LISTING

```
<160> NUMBER OF SEQ ID NOS: 72

<210> SEQ ID NO 1
<211> LENGTH: 6
<212> TYPE: PRT
<213> ORGANISM: Artificial Sequence
<220> FEATURE:
<223> OTHER INFORMATION: Synthesized

<400> SEQUENCE: 1

Pro Pro Tyr Asp Asp Asp
1               5

<210> SEQ ID NO 2
<211> LENGTH: 6
<212> TYPE: PRT
<213> ORGANISM: Artificial Sequence
<220> FEATURE:
<223> OTHER INFORMATION: Synthesized

<400> SEQUENCE: 2

Pro Pro Asp Asp Asp Asp
1               5

<210> SEQ ID NO 3
<211> LENGTH: 6
<212> TYPE: PRT
<213> ORGANISM: Artificial Sequence
<220> FEATURE:
<223> OTHER INFORMATION: Synthesized

<400> SEQUENCE: 3

Pro Pro Asp Gly Asp Asp
1               5

<210> SEQ ID NO 4
<211> LENGTH: 28
<212> TYPE: DNA
<213> ORGANISM: Artificial Sequence
<220> FEATURE:
<223> OTHER INFORMATION: Synthesized

<400> SEQUENCE: 4
ggggtaccat gaacgttcta cgcaagat                                    28

<210> SEQ ID NO 5
<211> LENGTH: 31
<212> TYPE: DNA
<213> ORGANISM: Artificial Sequence
<220> FEATURE:
<223> OTHER INFORMATION: Synthesized

<400> SEQUENCE: 5
cccaagcttt tattctagaa gcagagaaga g                                31

<210> SEQ ID NO 6
<211> LENGTH: 28
```

```
<212> TYPE: DNA
<213> ORGANISM: Artificial Sequence
<220> FEATURE:
<223> OTHER INFORMATION: Synthesized

<400> SEQUENCE: 6
ggggtaccat gaacgttcta cgcaagat                                   28

<210> SEQ ID NO 7
<211> LENGTH: 31
<212> TYPE: DNA
<213> ORGANISM: Artificial Sequence
<220> FEATURE:
<223> OTHER INFORMATION: Synthesized

<400> SEQUENCE: 7
cccaagctta ggtactggag ctcctgataa a                               31

<210> SEQ ID NO 8
<211> LENGTH: 29
<212> TYPE: DNA
<213> ORGANISM: Artificial Sequence
<220> FEATURE:
<223> OTHER INFORMATION: Synthesized

<400> SEQUENCE: 8
ggggtacctt atcaggagct ccagtacct                                  29

<210> SEQ ID NO 9
<211> LENGTH: 31
<212> TYPE: DNA
<213> ORGANISM: Artificial Sequence
<220> FEATURE:
<223> OTHER INFORMATION: Synthesized

<400> SEQUENCE: 9
cccaagcttt tattctagaa gcagagaaga g                               31

<210> SEQ ID NO 10
<211> LENGTH: 29
<212> TYPE: DNA
<213> ORGANISM: Artificial Sequence
<220> FEATURE:
<223> OTHER INFORMATION: Synthesized

<400> SEQUENCE: 10
ggggtaccat gaacgttcta cgcaagata                                  29

<210> SEQ ID NO 11
<211> LENGTH: 30
<212> TYPE: DNA
<213> ORGANISM: Artificial Sequence
<220> FEATURE:
<223> OTHER INFORMATION: Synthesized

<400> SEQUENCE: 11
cccaagcttc cacaggtcat cgtcatacgg                                 30

<210> SEQ ID NO 12
<211> LENGTH: 41
<212> TYPE: DNA
<213> ORGANISM: Artificial Sequence
<220> FEATURE:
<223> OTHER INFORMATION: Synthesized

<400> SEQUENCE: 12
```

-continued

```
ggggtacccc gtatgacgat gacctgtggc ttccacctcc t                        41

<210> SEQ ID NO 13
<211> LENGTH: 42
<212> TYPE: DNA
<213> ORGANISM: Artificial Sequence
<220> FEATURE:
<223> OTHER INFORMATION: Synthesized

<400> SEQUENCE: 13
cccaagctta ggaggtggaa gccacaggtc atcgtcatac gg                       42

<210> SEQ ID NO 14
<211> LENGTH: 28
<212> TYPE: DNA
<213> ORGANISM: Artificial Sequence
<220> FEATURE:
<223> OTHER INFORMATION: Synthesized

<400> SEQUENCE: 14
ggggtacctg acctgtggct tccacctc                                       28

<210> SEQ ID NO 15
<211> LENGTH: 31
<212> TYPE: DNA
<213> ORGANISM: Artificial Sequence
<220> FEATURE:
<223> OTHER INFORMATION: Synthesized

<400> SEQUENCE: 15
cccaagcttt tattctagaa gcagagaaga g                                   31

<210> SEQ ID NO 16
<211> LENGTH: 29
<212> TYPE: DNA
<213> ORGANISM: Artificial Sequence
<220> FEATURE:
<223> OTHER INFORMATION: Synthesized

<400> SEQUENCE: 16
ggggtaccat gaacgttcta cgcaagata                                      29

<210> SEQ ID NO 17
<211> LENGTH: 28
<212> TYPE: DNA
<213> ORGANISM: Artificial Sequence
<220> FEATURE:
<223> OTHER INFORMATION: Synthesized

<400> SEQUENCE: 17
tagggatgag gacactcaaa agcttggg                                       28

<210> SEQ ID NO 18
<211> LENGTH: 27
<212> TYPE: DNA
<213> ORGANISM: Artificial Sequence
<220> FEATURE:
<223> OTHER INFORMATION: Synthesized

<400> SEQUENCE: 18
ggggtaccca aaagccctct cctgtgt                                        27

<210> SEQ ID NO 19
<211> LENGTH: 30
<212> TYPE: DNA
<213> ORGANISM: Artificial Sequence
```

-continued

```
<220> FEATURE:
<223> OTHER INFORMATION: Synthesized

<400> SEQUENCE: 19
cccaagcttc cacaggtcat cgtcatacgg                                        30

<210> SEQ ID NO 20
<211> LENGTH: 29
<212> TYPE: DNA
<213> ORGANISM: Artificial Sequence
<220> FEATURE:
<223> OTHER INFORMATION: Synthesized

<400> SEQUENCE: 20
cgcccctccg tatgacgatg acctgtgga                                         29

<210> SEQ ID NO 21
<211> LENGTH: 37
<212> TYPE: DNA
<213> ORGANISM: Artificial Sequence
<220> FEATURE:
<223> OTHER INFORMATION: Synthesized

<400> SEQUENCE: 21
catggcgggg aggcatactg ctactggaca ccttcga                                37

<210> SEQ ID NO 22
<211> LENGTH: 30
<212> TYPE: DNA
<213> ORGANISM: Artificial Sequence
<220> FEATURE:
<223> OTHER INFORMATION: Synthesized

<400> SEQUENCE: 22
gatccgcccc tccgtatgac gatgacctgc                                        30

<210> SEQ ID NO 23
<211> LENGTH: 30
<212> TYPE: DNA
<213> ORGANISM: Artificial Sequence
<220> FEATURE:
<223> OTHER INFORMATION: Synthesized

<400> SEQUENCE: 23
tcgagcaggt catcgtcata cggaggggcg                                        30

<210> SEQ ID NO 24
<211> LENGTH: 27
<212> TYPE: DNA
<213> ORGANISM: Artificial Sequence
<220> FEATURE:
<223> OTHER INFORMATION: Synthesized

<400> SEQUENCE: 24
gatccgcccc tccgtatgac gatgacc                                           27

<210> SEQ ID NO 25
<211> LENGTH: 27
<212> TYPE: DNA
<213> ORGANISM: Artificial Sequence
<220> FEATURE:
<223> OTHER INFORMATION: Synthesized

<400> SEQUENCE: 25
tcgaggtcat cgtcatacgg aggggcg                                           27
```

-continued

```
<210> SEQ ID NO 26
<211> LENGTH: 24
<212> TYPE: DNA
<213> ORGANISM: Artificial Sequence
<220> FEATURE:
<223> OTHER INFORMATION: Synthesized

<400> SEQUENCE: 26
gatccgcccc tccgtatgac gatc                                              24

<210> SEQ ID NO 27
<211> LENGTH: 24
<212> TYPE: DNA
<213> ORGANISM: Artificial Sequence
<220> FEATURE:
<223> OTHER INFORMATION: Synthesized

<400> SEQUENCE: 27
tcgagatcgt catacggagg ggcg                                              24

<210> SEQ ID NO 28
<211> LENGTH: 21
<212> TYPE: DNA
<213> ORGANISM: Artificial Sequence
<220> FEATURE:
<223> OTHER INFORMATION: Synthesized

<400> SEQUENCE: 28
gatccgcccc tccgtatgac c                                                 21

<210> SEQ ID NO 29
<211> LENGTH: 21
<212> TYPE: DNA
<213> ORGANISM: Artificial Sequence
<220> FEATURE:
<223> OTHER INFORMATION: Synthesized

<400> SEQUENCE: 29
tcgaggtcat acggaggggc g                                                 21

<210> SEQ ID NO 30
<211> LENGTH: 30
<212> TYPE: DNA
<213> ORGANISM: Artificial Sequence
<220> FEATURE:
<223> OTHER INFORMATION: Synthesized

<400> SEQUENCE: 30
gatcccctcc gtatgacgat gacctgtggc                                        30

<210> SEQ ID NO 31
<211> LENGTH: 30
<212> TYPE: DNA
<213> ORGANISM: Artificial Sequence
<220> FEATURE:
<223> OTHER INFORMATION: Synthesized

<400> SEQUENCE: 31
tcgagccaca ggtcatcgtc atacggaggg                                        30

<210> SEQ ID NO 32
<211> LENGTH: 27
<212> TYPE: DNA
<213> ORGANISM: Artificial Sequence
<220> FEATURE:
<223> OTHER INFORMATION: Synthesized
```

-continued

<400> SEQUENCE: 32
gatccccgta tgacgatgac ctgtggc                                    27

<210> SEQ ID NO 33
<211> LENGTH: 27
<212> TYPE: DNA
<213> ORGANISM: Artificial Sequence
<220> FEATURE:
<223> OTHER INFORMATION: Synthesized

<400> SEQUENCE: 33
tcgagccaca ggtcatcgtc atacggg                                    27

<210> SEQ ID NO 34
<211> LENGTH: 24
<212> TYPE: DNA
<213> ORGANISM: Artificial Sequence
<220> FEATURE:
<223> OTHER INFORMATION: Synthesized

<400> SEQUENCE: 34
gatcctatga cgatgacctg tggc                                       24

<210> SEQ ID NO 35
<211> LENGTH: 24
<212> TYPE: DNA
<213> ORGANISM: Artificial Sequence
<220> FEATURE:
<223> OTHER INFORMATION: Synthesized

<400> SEQUENCE: 35
tcgagccaca ggtcatcgtc atag                                       24

<210> SEQ ID NO 36
<211> LENGTH: 21
<212> TYPE: DNA
<213> ORGANISM: Artificial Sequence
<220> FEATURE:
<223> OTHER INFORMATION: Synthesized

<400> SEQUENCE: 36
gatccgacga tgacctgtgg c                                          21

<210> SEQ ID NO 37
<211> LENGTH: 21
<212> TYPE: DNA
<213> ORGANISM: Artificial Sequence
<220> FEATURE:
<223> OTHER INFORMATION: Synthesized

<400> SEQUENCE: 37
tcgagccaca ggtcatcgtc g                                          21

<210> SEQ ID NO 38
<211> LENGTH: 6
<212> TYPE: PRT
<213> ORGANISM: Artificial Sequence
<220> FEATURE:
<223> OTHER INFORMATION: Synthesized

<400> SEQUENCE: 38

Pro Leu Tyr Asp Asp Asp
1               5

```
<210> SEQ ID NO 39
<211> LENGTH: 6
<212> TYPE: PRT
<213> ORGANISM: Artificial Sequence
<220> FEATURE:
<223> OTHER INFORMATION: Synthesized

<400> SEQUENCE: 39

Pro Pro Tyr Gly Asp Asp
1               5

<210> SEQ ID NO 40
<211> LENGTH: 41
<212> TYPE: PRT
<213> ORGANISM: Artificial Sequence
<220> FEATURE:
<223> OTHER INFORMATION: Synthesized

<400> SEQUENCE: 40

Met Asn Val Leu Arg Lys Ile Val Lys Lys Cys Arg Asp Glu Asp
1               5                   10                  15

Thr Gln Lys Pro Ser Pro Val Ser Ala Pro Pro Tyr Asp Asp Asp
            20                  25                  30

Leu Trp Leu Pro Pro Pro Glu Tyr Val Pro Leu
        35                  40

<210> SEQ ID NO 41
<211> LENGTH: 41
<212> TYPE: PRT
<213> ORGANISM: Artificial Sequence
<220> FEATURE:
<223> OTHER INFORMATION: Synthesized

<400> SEQUENCE: 41

Met Asn Phe Leu Cys Lys Ile Val Lys Asn Cys Arg Asp Glu Asp
1               5                   10                  15

Thr Gln Lys Pro Ser Pro Ala Ser Ala Pro Pro Asp Gly Asp Asp
            20                  25                  30

Leu Trp Leu Pro Pro Pro Glu Tyr Val Pro Leu
        35                  40

<210> SEQ ID NO 42
<211> LENGTH: 41
<212> TYPE: PRT
<213> ORGANISM: Artificial Sequence
<220> FEATURE:
<223> OTHER INFORMATION: Synthesized

<400> SEQUENCE: 42

Met Asn Phe Leu Cys Lys Ile Val Lys Asn Cys Arg Asp Glu Asp
1               5                   10                  15

Thr Gln Lys Pro Ser Pro Val Ser Ala Pro Pro Asp Gly Asp Asp
            20                  25                  30

Leu Trp Leu Pro Pro Pro Glu Tyr Val Pro Leu
        35                  40

<210> SEQ ID NO 43
<211> LENGTH: 41
<212> TYPE: PRT
<213> ORGANISM: Artificial Sequence
<220> FEATURE:
<223> OTHER INFORMATION: Synthesized

<400> SEQUENCE: 43
```

-continued

```
Met Asn Phe Leu Cys Lys Ile Val Lys Asn Cys Arg Asp Glu Asp
1               5                   10                  15

Thr Gln Lys Pro Ser Pro Ala Ser Ala Pro Pro Asp Gly Asp Asp
            20                  25                  30

Leu Trp Leu Pro Pro Pro Glu Tyr Val Pro Leu
        35                  40

<210> SEQ ID NO 44
<211> LENGTH: 41
<212> TYPE: PRT
<213> ORGANISM: Artificial Sequence
<220> FEATURE:
<223> OTHER INFORMATION: Synthesized

<400> SEQUENCE: 44

Met Asn Phe Leu Cys Lys Ile Val Lys Asn Cys Arg Asp Glu Asp
1               5                   10                  15

Thr Gln Lys Pro Ser Pro Ala Ser Ala Pro Pro Asp Gly Asp Asp
            20                  25                  30

Leu Trp Leu Pro Pro Pro Glu Tyr Val Pro Leu
        35                  40

<210> SEQ ID NO 45
<211> LENGTH: 41
<212> TYPE: PRT
<213> ORGANISM: Artificial Sequence
<220> FEATURE:
<223> OTHER INFORMATION: Synthesized

<400> SEQUENCE: 45

Met Asn Leu Leu Arg Lys Ile Val Lys Asn Arg Arg Asp Glu Asp
1               5                   10                  15

Thr Gln Lys Ser Ser Pro Ala Ser Ala Pro Leu Asp Asp Asp Asp
            20                  25                  30

Leu Trp Leu Pro Pro Pro Glu Tyr Val Pro Leu
        35                  40

<210> SEQ ID NO 46
<211> LENGTH: 41
<212> TYPE: PRT
<213> ORGANISM: Artificial Sequence
<220> FEATURE:
<223> OTHER INFORMATION: Synthesized

<400> SEQUENCE: 46

Met Asn Phe Leu Arg Lys Ile Val Lys Asn Cys Arg Asp Glu Asp
1               5                   10                  15

Thr Gln Lys Pro Ser Pro Val Ser Ala Pro Leu Asp Asp Asp Asp
            20                  25                  30

Leu Trp Leu Pro Pro Pro Glu Tyr Val Pro Leu
        35                  40

<210> SEQ ID NO 47
<211> LENGTH: 41
<212> TYPE: PRT
<213> ORGANISM: Artificial Sequence
<220> FEATURE:
<223> OTHER INFORMATION: Synthesized

<400> SEQUENCE: 47

Met Asn Phe Leu Arg Lys Ile Val Lys Asn Cys Arg Asp Glu Asp
1               5                   10                  15
```

```
Thr Gln Lys Pro Ser Pro Val Ser Ala Pro Pro Asp Asp Asp
        20              25              30

Leu Trp Leu Pro Pro Pro Glu Tyr Val Pro Leu
        35              40

<210> SEQ ID NO 48
<211> LENGTH: 41
<212> TYPE: PRT
<213> ORGANISM: Artificial Sequence
<220> FEATURE:
<223> OTHER INFORMATION: Synthesized

<400> SEQUENCE: 48

Met Asn Phe Leu Arg Lys Ile Val Lys Asn Cys Arg Asp Glu Asp
1               5               10              15

Thr Gln Lys Pro Ser Pro Thr Ser Ala Pro Pro Asp Asp Asp Asp
        20              25              30

Leu Trp Leu Pro Pro Pro Glu Tyr Val Pro Leu
        35              40

<210> SEQ ID NO 49
<211> LENGTH: 41
<212> TYPE: PRT
<213> ORGANISM: Artificial Sequence
<220> FEATURE:
<223> OTHER INFORMATION: Synthesized

<400> SEQUENCE: 49

Met Asn Phe Leu Arg Lys Ile Val Lys Asn Cys Arg Asp Glu Asp
1               5               10              15

Thr Gln Lys Pro Ser Leu Val Ser Ala Pro Pro Asp Asp Asp Asp
        20              25              30

Leu Trp Leu Pro Pro Pro Glu Tyr Val Pro Leu
        35              40

<210> SEQ ID NO 50
<211> LENGTH: 41
<212> TYPE: PRT
<213> ORGANISM: Artificial Sequence
<220> FEATURE:
<223> OTHER INFORMATION: Synthesized

<400> SEQUENCE: 50

Met Asn Phe Leu Arg Lys Ile Val Lys Lys Arg Lys Asp Glu Asp
1               5               10              15

Thr Gln Lys Pro Ser Pro Val Ser Ala Pro Pro Asp Asp Asp Asp
        20              25              30

Leu Trp Leu Pro Pro Pro Glu Tyr Val Pro Leu
        35              40

<210> SEQ ID NO 51
<211> LENGTH: 41
<212> TYPE: PRT
<213> ORGANISM: Artificial Sequence
<220> FEATURE:
<223> OTHER INFORMATION: Synthesized

<400> SEQUENCE: 51

Met Asn Phe Leu Arg Lys Ile Val Lys Asn Cys Arg Asp Glu Asp
1               5               10              15

Thr Gln Lys Pro Ser Pro Met Ser Ala Pro Pro Asp Asp Asp Asp
        20              25              30
```

```
Leu Trp Leu Pro Pro Pro Glu Tyr Val Pro Leu
        35                  40

<210> SEQ ID NO 52
<211> LENGTH: 41
<212> TYPE: PRT
<213> ORGANISM: Artificial Sequence
<220> FEATURE:
<223> OTHER INFORMATION: Synthesized

<400> SEQUENCE: 52

Met Asn Phe Leu Arg Lys Ile Val Lys Asn Cys Arg Asp Glu Asp
1               5                   10                  15

Pro Gln Lys Pro Ser Pro Met Ser Ala Pro Pro Asp Asp Asp Asp
            20                  25                  30

Leu Trp Leu Pro Pro Pro Glu Tyr Val Pro Leu
        35                  40

<210> SEQ ID NO 53
<211> LENGTH: 41
<212> TYPE: PRT
<213> ORGANISM: Artificial Sequence
<220> FEATURE:
<223> OTHER INFORMATION: Synthesized

<400> SEQUENCE: 53

Met Asn Phe Leu Arg Lys Ile Val Lys Asn Cys Arg Asp Glu Asp
1               5                   10                  15

Thr Gln Lys Pro Ser Pro Val Ser Ala Pro Pro Asp Asp Asp Asp
            20                  25                  30

Leu Trp Leu Pro Pro Pro Glu Tyr Val Pro Leu
        35                  40

<210> SEQ ID NO 54
<211> LENGTH: 41
<212> TYPE: PRT
<213> ORGANISM: Artificial Sequence
<220> FEATURE:
<223> OTHER INFORMATION: Synthesized

<400> SEQUENCE: 54

Met Asn Phe Leu Arg Lys Ile Val Lys Asn Cys Arg Tyr Glu Asp
1               5                   10                  15

Thr Gln Lys Pro Ser Ser Ala Ser Ala Pro Pro Asp Asp Asp Asp
            20                  25                  30

Leu Trp Leu Pro Pro Pro Glu Tyr Val Pro Leu
        35                  40

<210> SEQ ID NO 55
<211> LENGTH: 41
<212> TYPE: PRT
<213> ORGANISM: Artificial Sequence
<220> FEATURE:
<223> OTHER INFORMATION: Synthesized

<400> SEQUENCE: 55

Met Asn Phe Leu Arg Lys Ile Val Lys Asn Cys Arg Asp Glu Asp
1               5                   10                  15

Thr Gln Lys Pro Ser Ser Val Ser Ala Pro Pro Asp Asp Asp Asp
            20                  25                  30

Leu Trp Leu Pro Pro Pro Glu Tyr Ile Pro Leu
        35                  40
```

```
<210> SEQ ID NO 56
<211> LENGTH: 41
<212> TYPE: PRT
<213> ORGANISM: Artificial Sequence
<220> FEATURE:
<223> OTHER INFORMATION: Synthesized

<400> SEQUENCE: 56

Met Asn Phe Leu Arg Lys Ile Val Lys Asn Cys Arg Asp Glu Asp
1               5                   10                  15

Thr Gln Lys Pro Ser Pro Val Ser Ala Pro Pro Asp Asp Asp Asp
            20                  25                  30

Leu Trp Leu Pro Pro Pro Glu Tyr Val Pro Leu
        35                  40

<210> SEQ ID NO 57
<211> LENGTH: 41
<212> TYPE: PRT
<213> ORGANISM: Artificial Sequence
<220> FEATURE:
<223> OTHER INFORMATION: Synthesized

<400> SEQUENCE: 57

Met Asn Phe Leu Arg Lys Ile Val Lys Asn Cys Arg Asp Glu Asp
1               5                   10                  15

Thr Gln Lys Pro Ser Pro Val Ser Ala Pro Pro Asp Asp Asp Asp
            20                  25                  30

Leu Trp Leu Pro Pro Pro Glu Tyr Val Pro Leu
        35                  40

<210> SEQ ID NO 58
<211> LENGTH: 41
<212> TYPE: PRT
<213> ORGANISM: Artificial Sequence
<220> FEATURE:
<223> OTHER INFORMATION: Synthesized

<400> SEQUENCE: 58

Met Asn Phe Leu Arg Lys Ile Val Lys Asn Cys Arg Asp Glu Asp
1               5                   10                  15

Thr Gln Lys Pro Ser Ser Val Ser Ala Pro Pro Asp Asp Asp Asp
            20                  25                  30

Leu Trp Leu Pro Pro Pro Glu Tyr Val Pro Leu
        35                  40

<210> SEQ ID NO 59
<211> LENGTH: 41
<212> TYPE: PRT
<213> ORGANISM: Artificial Sequence
<220> FEATURE:
<223> OTHER INFORMATION: Synthesized

<400> SEQUENCE: 59

Met Asn Phe Leu Arg Lys Ile Val Lys Asn Cys Lys Asp Glu Asp
1               5                   10                  15

Thr His Lys Pro Ser Pro Ala Ser Ala Pro Pro Asp Asp Asp Asp
            20                  25                  30

Leu Trp Leu Pro Pro Pro Glu Tyr Val Pro Leu
        35                  40

<210> SEQ ID NO 60
<211> LENGTH: 41
```

```
<212> TYPE: PRT
<213> ORGANISM: Artificial Sequence
<220> FEATURE:
<223> OTHER INFORMATION: Synthesized

<400> SEQUENCE: 60

Met Asn Phe Leu Arg Lys Ile Val Lys Asn Cys Arg Asp Glu Asp
1               5                   10                  15

Thr Gln Lys Pro Ser Pro Val Ser Ala Pro Pro Asp Asp Asp Asp
            20                  25                  30

Leu Trp Leu Pro Pro Pro Glu Tyr Val Pro Leu
        35                  40

<210> SEQ ID NO 61
<211> LENGTH: 41
<212> TYPE: PRT
<213> ORGANISM: Artificial Sequence
<220> FEATURE:
<223> OTHER INFORMATION: Synthesized

<400> SEQUENCE: 61

Met Asn Phe Leu Arg Lys Ile Val Lys Asn Cys Arg Asp Glu Asp
1               5                   10                  15

Thr Gln Lys Pro Phe Ser Val Ser Ala Pro Pro Asp Asp Asp Asp
            20                  25                  30

Leu Trp Leu Pro Pro Pro Glu Tyr Val Pro Leu
        35                  40

<210> SEQ ID NO 62
<211> LENGTH: 41
<212> TYPE: PRT
<213> ORGANISM: Artificial Sequence
<220> FEATURE:
<223> OTHER INFORMATION: Synthesized

<400> SEQUENCE: 62

Met Asn Phe Leu Arg Lys Ile Val Lys Asn Cys Arg Asp Glu Asp
1               5                   10                  15

Thr His Lys Pro Phe Ser Ala Ser Ala Pro Pro Asp Asp Asp Asp
            20                  25                  30

Leu Trp Leu Pro Pro Pro Glu Tyr Val Pro Leu
        35                  40

<210> SEQ ID NO 63
<211> LENGTH: 41
<212> TYPE: PRT
<213> ORGANISM: Artificial Sequence
<220> FEATURE:
<223> OTHER INFORMATION: Synthesized

<400> SEQUENCE: 63

Met Asn Phe Leu Arg Lys Ile Val Lys Asn Cys Arg Asp Glu Asp
1               5                   10                  15

Thr Gln Lys Pro Ser Pro Val Ser Ala Pro Pro Asp Asp Asp Asp
            20                  25                  30

Leu Trp Leu Pro Pro Pro Glu Tyr Val Pro Leu
        35                  40

<210> SEQ ID NO 64
<211> LENGTH: 41
<212> TYPE: PRT
<213> ORGANISM: Artificial Sequence
<220> FEATURE:
```

35

36

-continued

```
<223> OTHER INFORMATION: Synthesized

<400> SEQUENCE: 64

Met Asn Phe Leu Arg Lys Ile Val Lys Asn Cys Arg Asp Glu Asp
1               5                   10                  15

Thr His Lys Pro Phe Ser Ala Ser Ala Pro Pro Asp Asp Asp Asp
            20                  25                  30

Leu Trp Leu Pro Pro Pro Glu Tyr Val Pro Leu
        35                  40

<210> SEQ ID NO 65
<211> LENGTH: 41
<212> TYPE: PRT
<213> ORGANISM: Artificial Sequence
<220> FEATURE:
<223> OTHER INFORMATION: Synthesized

<400> SEQUENCE: 65

Met Asn Phe Leu Arg Lys Ile Val Lys Asn Cys Arg Asp Glu Asp
1               5                   10                  15

Thr Gln Lys Pro Phe Ser Ala Ser Ala Pro Pro Asp Asp Asp Asp
            20                  25                  30

Leu Trp Leu Pro Pro Pro Glu Tyr Val Pro Leu
        35                  40

<210> SEQ ID NO 66
<211> LENGTH: 41
<212> TYPE: PRT
<213> ORGANISM: Artificial Sequence
<220> FEATURE:
<223> OTHER INFORMATION: Synthesized

<400> SEQUENCE: 66

Met Asn Phe Leu Arg Lys Ile Val Lys Asn Cys Arg Asp Glu Asp
1               5                   10                  15

Thr Gln Lys Pro Ser Pro Val Ser Ala Pro Pro Asp Asp Asp Asp
            20                  25                  30

Leu Trp Leu Pro Pro Pro Glu Tyr Val Pro Leu
        35                  40

<210> SEQ ID NO 67
<211> LENGTH: 41
<212> TYPE: PRT
<213> ORGANISM: Artificial Sequence
<220> FEATURE:
<223> OTHER INFORMATION: Synthesized

<400> SEQUENCE: 67

Met Asn Phe Leu Arg Lys Ile Val Lys Asn Cys Arg Asp Glu Asp
1               5                   10                  15

Thr Gln Lys Pro Ser Pro Val Ser Ala Pro Pro Asp Asp Asp Asp
            20                  25                  30

Leu Trp Leu Pro Pro Pro Glu Tyr Val Pro Leu
        35                  40

<210> SEQ ID NO 68
<211> LENGTH: 41
<212> TYPE: PRT
<213> ORGANISM: Artificial Sequence
<220> FEATURE:
<223> OTHER INFORMATION: Synthesized

<400> SEQUENCE: 68
```

```
Met Asn Phe Leu Arg Lys Ile Val Lys Asn Cys Arg Asp Glu Asp
1               5                   10                  15

Thr Gln Lys Pro Ser Pro Val Ser Ala Pro Pro Asp Asp Asp
            20                  25                  30

Leu Trp Leu Pro Pro Pro Glu Tyr Val Pro Leu
        35                  40
```

<210> SEQ ID NO 69
<211> LENGTH: 41
<212> TYPE: PRT
<213> ORGANISM: Artificial Sequence
<220> FEATURE:
<223> OTHER INFORMATION: Synthesized

<400> SEQUENCE: 69

```
Met Asn Phe Leu Arg Lys Ile Val Lys Asn Cys Arg Asp Glu Asp
1               5                   10                  15

Thr His Lys Pro Phe Ser Ala Ser Ala Pro Pro Asp Asp Asp Asp
            20                  25                  30

Leu Trp Leu Pro Pro Pro Glu Tyr Val Pro Leu
        35                  40
```

<210> SEQ ID NO 70
<211> LENGTH: 41
<212> TYPE: PRT
<213> ORGANISM: Artificial Sequence
<220> FEATURE:
<223> OTHER INFORMATION: Synthesized

<400> SEQUENCE: 70

```
Met Asn Phe Leu Arg Lys Ile Val Lys Asn Cys Arg Asp Glu Asp
1               5                   10                  15

Thr His Lys Pro Phe Ser Ala Ser Ala Pro Pro Asp Asp Asp Asp
            20                  25                  30

Leu Trp Leu Pro Pro Pro Glu Tyr Val Pro Leu
        35                  40
```

<210> SEQ ID NO 71
<211> LENGTH: 41
<212> TYPE: PRT
<213> ORGANISM: Artificial Sequence
<220> FEATURE:
<223> OTHER INFORMATION: Synthesized

<400> SEQUENCE: 71

```
Met Asn Phe Leu Arg Lys Ile Val Lys Asn Cys Arg Asp Glu Asp
1               5                   10                  15

Thr His Lys Pro Phe Ser Ala Ser Ala Pro Pro Asp Asp Asp Asp
            20                  25                  30

Leu Trp Leu Pro Pro Pro Glu Tyr Val Pro Leu
        35                  40
```

<210> SEQ ID NO 72
<211> LENGTH: 41
<212> TYPE: PRT
<213> ORGANISM: Artificial Sequence
<220> FEATURE:
<223> OTHER INFORMATION: Synthesized

<400> SEQUENCE: 72

```
Met Asn Phe Leu Arg Lys Ile Val Lys Asn Cys Arg Asp Glu Asp
1               5                   10                  15
```

-continued

```
Thr Gln Lys Pro Ser Pro Ala Ser Ala Pro Pro Asp Asp Asp Asp
        20                  25                  30

Leu Trp Leu Pro Pro Pro Glu Tyr Val Pro Leu
        35                  40
```